United States Patent [19]

Chou

[11] 4,212,977
[45] Jul. 15, 1980

[54] PROCESS FOR PREPARING N-CHLOROIMIDES

[75] Inventor: Ta-Sen Chou, Indianapolis, Ind.

[73] Assignee: Eli Lilly and Company, Indianapolis, Ind.

[21] Appl. No.: 971,617

[22] Filed: Dec. 20, 1978

[51] Int. Cl.$^2$ .................. C07D 211/92; C07D 209/48; C07D 207/46
[52] U.S. Cl. ............................. 546/243; 260/326 HL; 260/326.5 FM
[58] Field of Search .............. 260/326 HL, 326.5 FM; 546/243

[56] References Cited

U.S. PATENT DOCUMENTS

| | | | |
|---|---|---|---|
| 2,686,203 | 8/1954 | Hechenbleikner | 260/694 |
| 4,082,766 | 4/1978 | Chou et al. | 260/326 HL |

FOREIGN PATENT DOCUMENTS

| | | | |
|---|---|---|---|
| 139553 | 12/1901 | Fed. Rep. of Germany | 260/326 HL |
| 161340 | 4/1902 | Fed. Rep. of Germany | 260/326 HL |
| 20801 | of 1898 | United Kingdom | 260/326 HL |

OTHER PUBLICATIONS

M. L. Hallensleben et al., Angew. Chem. Int. Ed. Engl., vol. 15, (1976), No. 3, p. 163.

Primary Examiner—Norma S. Milestone
Attorney, Agent, or Firm—David E. Frankhouser; Arthur R. Whale

[57] ABSTRACT

N-chlorophthalimide, N-chlorosuccinimide, and N-chloroglutarimide are prepared by contacting the corresponding imide with molecular chlorine under substantially non-aqueous conditions in an inert organic solvent in the presence of a poly(4-vinylpyridine)-divinylbenzene copolymer.

4 Claims, No Drawings

PROCESS FOR PREPARING N-CHLOROIMIDES

This invention relates to a process for the manufacture of N-chlorophthalimide, N-chlorosuccinimide, or N-chloroglutarimide.

The principal prior art processes for preparing N-chloroimides customarily have employed an aqueous reaction medium. In general, such processes can be classified as follows:

(1) Chlorination of the corresponding imide using an inorganic hypochlorite in a mixture of acetic acid and water;

(2) Chlorination by passing chlorine into an aqueous solution comprising equivalent amounts of the corresponding imide and a strong base, e.g., sodium hydroxide or potassium hydroxide;

(3) Chlorination of the corresponding imide using t-butyl hypochlorite in a mixture of t-butyl alcohol and water.

Of the above general methods, only method (2) involves the use of molecular chlorine. However, because of the presence of the aqueous system, this method has been found to have serious drawbacks. First, chlorine is only very slightly soluble in water. Secondly, and more importantly, it is known that an imide, when present in an alkaline aqueous medium such as would result from potassium or sodium hydroxide and water, undergoes rapid hydrolysis. When, for example, phthalimide is subjected to alkaline aqueous conditions, the following decomposition sequence occurs:

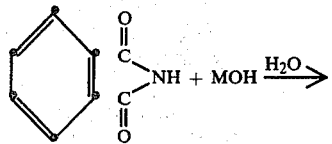

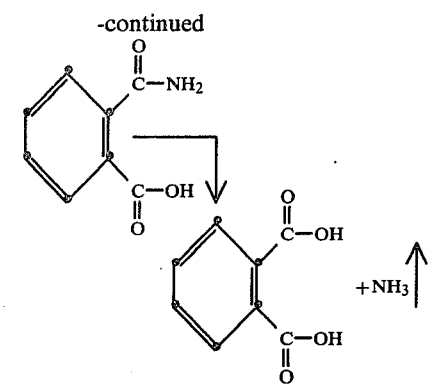

Even more importantly, it has been established [Arthur R. Hurwitz, "Degradation of N-Chlorosuccinimide in Aqueous Solution", *Diss. Abst.*, B, 28 (3), 971 (1967)] that an N-chloroimide product, when present in an aqueous alkaline medium, such as would be the case under the conditions of chlorination provided by method (2) above, degrades with possible formation of the highly explosive and toxic gas, nitrogen trichloride. The following sequences are postulated for the decomposition of N-chlorosuccinimide:

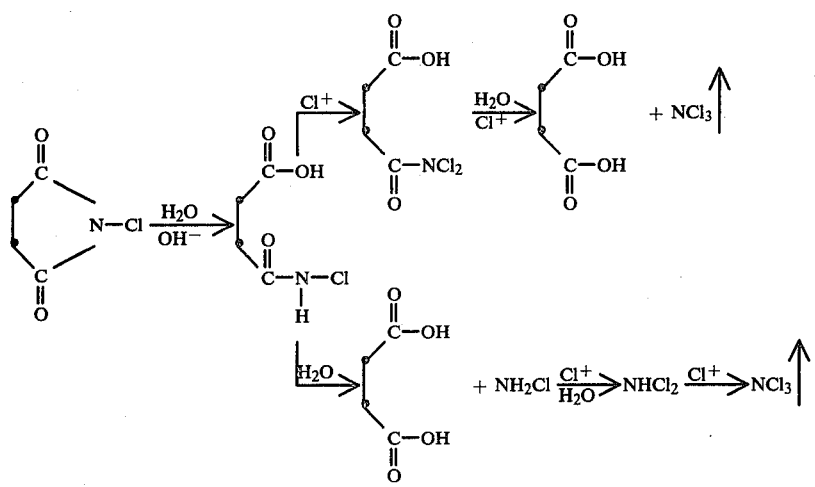

Non-aqueous processes for preparing N-chloro compounds have been few. U.S. Pat. No. 2,686,203 describes a process for preparing N-halo-t-alkyl cyanamides by treating a t-alkyl cyanamide with molecular chlorine in an inert solvent in the presence of a molar equivalent of a halogen acid acceptor, typically pyridine. U.S Pat. No. 4,082,766 discloses a method for preparing N-chlorophthalimide under substantially non-aqueous reaction conditions by contacting an alkali metal salt of phthalimide with chlorine in the presence of a halogenated aliphatic hydrocarbon at a temperature of from about $-10°$ C. to about $+40°$ C.

An even more advantageous method employs a substantially non-aqueous medium and permits use of the imide itself as starting material instead of the previously required alkali metal salt. The N-chloroimide is prepared by contacting the corresponding imide with molecular chlorine at a temperature of from about $-10°$ C. to about $+50°$ C. under substantially non-aqueous conditions in the presence of (1) an epoxy compound in an amount representing at least about one epoxy moiety per each imide moiety and (2) at least a catalytic amount of a tertiary amine. This method is the subject of copending application of T. S. Chou Ser. No. 861,582, filed Dec. 19, 1977.

The invention sought to be patented constitutes a process for preparing N-chlorophthalimide, N-chlorosuccinimide or N-chloroglutarimide which comprises contacting phthalimide, succinimide, or glutarimide with molecular chlorine at a temperature of from about −10° C. to about 50° C. under substantially non-aqueous conditions in the presence of poly(4-vinylpyridine)-divinylbenzene copolymer in a ratio by weight of said copolymer to phthalimide, succinimide, or glutarimide of between 1:1 and about 1:5, said copolymer containing between about 1% to about 10% cross linking.

The poly(4-vinylpyridine)-divinyl benzene copolymer is weakly basic and is insoluble in organic solvents. the copolymer effects the rapid removal of hydrogen chloride from the reaction medium and shifts the reaction equilibrium to favor N-chloroimide formation. Further, the 4-vinylpyridine-divinylbenzene copolymer is readily removed from the reaction medium by filtration or other suitable means.

Whereas the use of an epoxy compound for removing hydrogen chloride during the reaction of an imide with chlorine require the presence of a tertiary amine catalyst (e.g. quinoline), as described in the aforesaid copending application Ser. No. 861,582, the use of the 4-vinylpyridine-divinylbenzene copolymer does not require the use of a tertiary amine catalyst. Comparable yields are obtained in the process with or without a tertiary amine catalyst.

In practicing the process of the invention, the chlorine can be introduced into the reaction medium containing the desired imide either by passing the gas directly into the reaction medium or by first absorbing chlorine onto the polymer and then adding the polymer-chlorine complex to the reaction medium. It will be understood that both techniques are within the scope of the invention.

In the reaction of chlorine with the imide moiety one mole of chlorine is consumed for each mole of available imide moiety. Therefore, it is highly preferred that at least one mole of chlorine is present per each mole of imide moiety. Even more preferably, about a 10% molar excess of chlorine is brought into contact with the imide. The temperature at which the reaction is carried out generally ranges from about −10° C. to about +50° C. and, preferably, from about −5° C. to about +25° C. The reaction generally is completed after a period of from about 1 hour to about 24 hours, and, preferably, is carried out over a period of from about 3 to 15 hours.

The reaction between the imide and chlorine is carried out in an inert organic solvent under substantially non-aqueous conditions. The term "substantially non-aqueous conditions" does not mean the total absence of water from the reaction system; instead, this term prescribes the exercise of reasonable precautions to ensure its preclusion, including the avoidance of any deliberate addition of water to the reaction medium prior to or during the time in which the reaction is being effected. Amounts of water which are customarily present in such commercial solvents and reactants as may be employed in the process of this invention need not first be removed in order to comply with the "substantially non-aqueous" requirement. By the term "solvent" is meant a medium which partially or completely solubilizes the imide starting material. The term "inert" defines a solvent which generally does not react with the reactants, principally, with the chlorine, under the conditions of the process. Typical such solvents are halogenated aromatic and aliphatic hydrocarbons. Examples of halogenated aromatic hydrocarbons are chlorobenzene, 1,2-dichlorobenzene, 1,4-dichlorobenzene, bromobenzene, and the like. Examples of halogenated aliphatic hydrocarbons are methylene chloride, chloroform, 1,1,2-trichloroethane, 1,2-dichloroethane, 1,1-dichloroethane, 1,1,1-trichloroethane, and the like. Of the above, the halogenated aliphatic hydrocarbons are preferred, and, of these, the preferred solvent is methylene chloride.

The copolymeric resin of 4-vinylpyridine and divinylbenzene employed in the process of this invention is a weakly basic resin which is insoluble in the inert organic solvents and in particular, the reaction medium employed in the present process. The polymer contains cross-linking of from about 1% to about 10% based on the weight of polymer. The cross-linked poly(4-vinylpyridine) polymer is prepared with divinylbenzene as described by Hallensleben and Wurm, *Angew. Chem. Int. Ed. Engl.* 15, 163 (1976). Alternatively the cross-linked polymer can be prepared in water via emulsion polymerization with surfactants such as polyvinyl alcohol or polyethylene oxide. Macroreticular beads of the cross-linked polymer can be prepared by procedures known in the art, for example, as described by U.S. Pat. No. 3,816,355.

The preferred extent of cross-linking in the polymer is between about 2% and about 5%. The desired range of cross-linking is obtained by using the appropriate amount of divinylbenzene in the polymerization of the 4-vinylpyridine. The poly(4-vinylpyridine) having the desired cross-linking rapidly absorbs the hydrogen chloride formed during the reaction of the phthalimide, succinimide or glutarimide with chlorine. Further, since the polymer is insoluble in the reaction medium, the acid is rapidly and completely removed from the reaction system. This rapid removal of the acid side product shifts the equilibrium of the reaction to favor chlorination.

The cross-linked poly(4-vinylpyridine) can be used in a variety of forms. For example, it can be in the form of a fine powder or in the form of small beads, or in the form of macroporous beads. Preferably the form of the copolymer has a high surface area which is a measure of the availability of the basic sites of the polymer to the acid. Accordingly, the lower the average particle size of the polymer the higher will be the surface area and the greater availability of basic groups. Likewise, the copolymer in the form of macroporous beads has a high surface area including internal surface area with concomitant high exposure of the basic groups in the copolymer. For copolymer in the form of relatively uniform shape such as bead shaped, for example macroreticular beads, the preferred size is between about 20 microns and about 120 microns in diameter. For copolymer of irregular particle shape, such as may be obtained by crushing the copolymer resin in a hammer mill, the preferred particle size is obtained by collecting the particles passing through a sieve of about 120 mesh.

Copolymer having the cross-linking content of between about 1% and about 10% displays characteristic swelling in the organic solvents employed in the process. Copolymer having a higher cross-linking content swells to a lesser degree and, the extent of swelling decreases as the extent of cross-linking increases. The increased volume of the copolymer due to swelling allows for greatly enhanced access to the basic sites in the polymer by hydrogen chloride. Copolymers which are cross-linked to greater than 10% swell much less than those which are cross-linked to less than 10%, or within the preferred range, and although insoluble in the organic solvents are not efficient HCl binders.

The ratio of the amount of polymer employed per amount of imide starting material is between about 1:1 and about 1:5 by weight. Preferably, the ratio is about 1:2 to about 1:3.

N-chlorophthalimide, N-chlorosuccinimide and N-chloroglutarimide produced by the process of this invention are highly useful reagents for carrying out chlorination reactions which require a source of positive chlorine. Examples of such reactions are, for example, oxidation of sulfides, alcohols, amines, and imines; chlorination of amines, reactive aromatic systems, carbonyl compounds having $\alpha$-hydrogens, and the like.

The following examples further illustrate the process of this invention.

EXAMPLE 1

Preparation of poly(4-vinylpyridine)-divinylbenzene copolymer

To a 2-liter, 3-necked round bottom flask were added 1100 ml. of water and 4.8 g. of poly(vinyl alcohol) and the solution was heated under nitrogen to 80° C. A solution of 50 g. of 4-vinylpyridine and 3.0 g. of divinylbenzene in 100 ml. of toluene was rapidly added with stirring to the hot solution, followed by the addition of 2 g. of azobisisobutyronitrile. The copolymer began to form at once and the suspension was stirred vigorously at 80° C. for about 16 hours.

The copolymer was collected by filtering the reaction mixture through cloth and was washed extensively with water, acetone, diethyl ether, methylene chloride and lastly with methyl alcohol. Swelling was encountered during the diethyl ether washing and with the methylene chloride and methyl alcohol washings. The copolymeric resin was then dried in vacuo to yield 45.05 g. of the dried resin.

The resin was finished by grinding and collecting the material which passed through 60 mesh sieve.

The nitrogen content of the resin was 12.35% as determined by combustion.

EXAMPLE 2

N-Chlorophthalimide (Method A)

To 2.45 g. of 4-vinylpyridine-divinylbenzene copolymer (7.38 mcg./g., 10% excess) in 200 ml. of methylene chloride was introduced chlorine until the solvent turned slightly greenish yellow. Phthalimide (7.35 g, 50 mM) was added in one portion. Quinoline (three drops) was added, and the reaction mixture was stirred at room temperature for five hours.

The reaction mixture was filtered to remove reacted and unreacted polymer. The polymer was washed twice with methylene chloride (15 ml.). The original filtrate and the washing were combined and evaporated slowly to about one-third volume. White crystals formed at this step, but the mixture was kept in a refrigerator overnight to complete the crystallization. The crystals were collected by filtration. After drying under vacuum, there was obtained 8.70 g. (95.9% yield) of the title product, m.p. 179.5°–180° C., identified by infrared spectral analysis. Percent chlorine: Found 17.6; calculated 19.5%.

Repeating the above procedure but omitting the quinoline catalyst there was obtained 8.05 g. of the title product, m.p. 180°–183° C. (Yield 88.7%). Percent chlorine: Found, 10.7; calculated 19.5%. The infrared spectra of the product is identical to that obtained above.

EXAMPLE 3

N-Chlorophthalimide (Method B)

To 7.45 g. of 4-vinylpyridine-divinylbenzene copolymer (55 mM/eg), in 100 ml. of methylene chloride, was added chlorine until there was produced a persistent yellow color in the solvent. The polymer was collected by filtration under slight vacuum. The wet polymer-chlorine complex was then placed in 100 ml. of phthalimide (7.35 g.). The mixture was stirred at room temperature for three hours. By thin layer chromatography, it was shown that at least 50% of the phthalimide is converted to the N-chlorinated product.

What is claimed is:

1. A process for preparing N-chlorophthalimide, N-chlorosuccinimide, or N-chloroglutarimide comprising contacting phthalimide, succinimide or glutarimide with chlorine at a temperature or from about −10° C. to about +50° C. under substantially non-aqueous conditions in the presence of poly(4-vinylpyridine)-divinylbenzene copolymer in a ratio by weight of said copolymer to phthalimide, succinimide, or glutarimide of between 1:1 and about 1:5, said copolymer containing between about 1% and about 10% cross linking.

2. A process as defined in claim 1 wherein N-chlorophthalimide is prepared.

3. A process as defined in claim 1 wherein N-chlorosuccinimide is prepared.

4. A process as defined in claim 1 wherein N-chloroglutarimide is prepared.

* * * * *